(12) United States Patent
Pawlak

(10) Patent No.: US 10,995,789 B2
(45) Date of Patent: May 4, 2021

(54) MULTI-FEATURED PANEL FASTENER AND PANEL SYSTEM INCLUDING THE MULTI-FEATURED PANEL FASTENER

(71) Applicant: ARMSTRONG WORLD INDUSTRIES, INC., Lancaster, PA (US)

(72) Inventor: Samuel D. Pawlak, Lancaster, PA (US)

(73) Assignee: AWI Licensing LLC, Wilmington, DE (US)

( * ) Notice: Subject to any disclaimer, the term of this patent is extended or adjusted under 35 U.S.C. 154(b) by 308 days.

(21) Appl. No.: 16/123,127

(22) Filed: Sep. 6, 2018

(65) Prior Publication Data

US 2019/0072124 A1 Mar. 7, 2019

Related U.S. Application Data

(60) Provisional application No. 62/554,780, filed on Sep. 6, 2017.

(51) Int. Cl.
*F16B 25/00* (2006.01)
*E04F 13/08* (2006.01)
(Continued)

(52) U.S. Cl.
CPC ...... *F16B 25/0031* (2013.01); *E04F 13/0801* (2013.01); *E04F 13/0837* (2013.01);
(Continued)

(58) Field of Classification Search
CPC ........ F16B 5/02; F16B 5/0208; F16B 5/0275; F16B 25/00; F16B 25/0031;
(Continued)

(56) References Cited

U.S. PATENT DOCUMENTS

| 422,307 A | * | 2/1890 | Libbey | ................... F16B 25/00 411/412 |
| 1,863,496 A | * | 6/1932 | Mooney | ................... B60B 3/18 301/35.627 |

(Continued)

FOREIGN PATENT DOCUMENTS

| CA | 2318795 A1 | 8/1999 |
| EP | 2096231 A | 9/2009 |

(Continued)

OTHER PUBLICATIONS

International Search Report for Related Application No. PCT/US2018/049660, dated Jan. 2, 2019.

*Primary Examiner* — Roberta S Delisle
(74) *Attorney, Agent, or Firm* — Craig M. Sterner

(57) ABSTRACT

A panel fastener is provided that has a head having a first surface and a second surface opposite the first surface; an engagement feature on the first surface of the head, the engagement feature being configured to be engaged by a driving tool; a shank extending from the second surface of the head; a threaded portion extending from the shank, the threaded portion having first and second helical threads arranged in an intertwined manner; the first thread extending farther radially from the central axis than does the second thread; and the shank being located between the head and the threaded portion.

18 Claims, 8 Drawing Sheets

(51) Int. Cl.
*F16B 5/02* (2006.01)
*F16B 35/04* (2006.01)
*F16B 35/06* (2006.01)
*F16B 25/10* (2006.01)

(52) U.S. Cl.
CPC .............. *F16B 5/02* (2013.01); *F16B 5/0208* (2013.01); *F16B 25/106* (2013.01); *F16B 35/041* (2013.01); *F16B 35/06* (2013.01); *F16B 25/00* (2013.01)

(58) Field of Classification Search
CPC .... F16B 25/0068; F16B 25/106; F16B 33/02; F16B 35/041; F16B 35/06; E04F 13/0801; E04F 13/0837
USPC .......................................... 411/411, 412, 424
See application file for complete search history.

(56) References Cited

U.S. PATENT DOCUMENTS

| | | | | |
|---|---|---|---|---|
| 2,147,013 A | * | 2/1939 | Danly | F16B 35/041 411/384 |
| 3,023,797 A | * | 3/1962 | Greene | F16B 37/122 411/106 |
| 3,296,694 A | * | 1/1967 | De Mastry | B23P 11/005 29/520 |
| 3,746,067 A | * | 7/1973 | Gulistan | F16B 43/00 411/361 |
| 4,577,402 A | * | 3/1986 | Swanstrom | H01L 23/4006 174/16.3 |
| 4,655,658 A | * | 4/1987 | Gulistan | F16B 41/002 29/437 |
| 4,655,661 A | | 4/1987 | Brandt | |
| 5,178,500 A | * | 1/1993 | Stencel | F16B 39/34 29/456 |
| 5,183,286 A | * | 2/1993 | Ayabe | B60G 7/02 280/124.1 |
| 5,253,966 A | * | 10/1993 | Clemens | F02M 35/10072 249/165 |
| 5,540,531 A | * | 7/1996 | Choiniere | F16B 25/0031 411/387.1 |
| 5,755,542 A | * | 5/1998 | Janusz | F16B 33/06 411/387.4 |
| 6,053,653 A | * | 4/2000 | Tanaka | F16B 5/0275 29/525.11 |
| 6,601,885 B1 | * | 8/2003 | Yiu | E05B 79/04 292/337 |
| 6,907,699 B2 | * | 6/2005 | Schmid | F16B 23/0007 411/394 |
| 6,923,611 B2 | * | 8/2005 | Kenny | F16B 25/0031 411/387.1 |
| 7,293,947 B2 | | 11/2007 | Craven | |
| 7,334,374 B2 | * | 2/2008 | Schmid | F16B 35/041 411/399 |
| 8,641,344 B1 | * | 2/2014 | Avetisian | F16B 39/32 411/347 |
| 2003/0219328 A1 | * | 11/2003 | Schultz | F16B 33/06 411/378 |
| 2005/0058525 A1 | * | 3/2005 | Bakos | F16B 35/048 411/424 |
| 2007/0292236 A1 | | 12/2007 | Hsieh | |
| 2011/0033262 A1 | * | 2/2011 | Gulistan | F16B 5/0208 411/347 |
| 2011/0091298 A1 | * | 4/2011 | Bowers | F16B 43/00 411/103 |
| 2011/0170983 A1 | * | 7/2011 | Day | F16B 39/24 411/370 |
| 2015/0078860 A1 | * | 3/2015 | Ellingson | F16B 33/02 411/368 |
| 2015/0240477 A1 | | 8/2015 | Weeks et al. | |

FOREIGN PATENT DOCUMENTS

| | | |
|---|---|---|
| FR | 2676244 A1 | 11/1992 |
| GB | 2376995 B | 2/2004 |
| JP | 2001-090719 A | 4/2001 |
| JP | 2001-280318 A | 10/2001 |
| JP | 2003-322122 A | 11/2003 |
| JP | 2004084244 A | 3/2004 |
| JP | 2004-176900 A | 6/2004 |

* cited by examiner

MULTI-FEATURED PANEL FASTENER AND PANEL SYSTEM INCLUDING THE MULTI-FEATURED PANEL FASTENER

CROSS-REFERENCE TO RELATED APPLICATIONS

This application claims the benefit of U.S. Provisional Application No. 62/554,780, filed on Sep. 6, 2017. The disclosure of the above application is incorporated herein by reference.

FIELD

The present invention relates to building panel systems. Particular embodiments of the invention relate to a fastener for attaching panels to a framework to form a ceiling, wall, or other barrier. Other embodiments of the invention relate to a building panel system using the inventive fastener.

BACKGROUND

Many types of ceiling systems and methods for mounting ceiling panels have been used. Several types of system use a suspended metal support grid or other structure to which panels are fastened. The panels can be many different compositions. Some panels are made from a fibrous or other material that can be easily compressed and permanently deforms. Many acoustical ceiling and wall panels are made of such a material.

A problem exists in that is can be difficult to securely fasten an easily compressed ceiling or wall panel to a supporting structure without deforming the panel. For example, a conventional screw can easily be driven too far into such a panel resulting in permanent deformation of the panel and, in some cases, insufficient holding power that can ultimately result in the panel not being securely fastened to the structure due to the head of the screw being pulled through the panel. Also, it can also be very difficult to drive conventional screws to a uniform depth so that the heads are all at the same elevation relative to an outward face of the panel.

Accordingly, improved systems and methods for fastening a ceiling or wall panel to a supporting structure are provided by the invention. These systems and methods provide a fastener that is easily driven to a uniform depth relative to the outward face of the panel without deforming the panel.

SUMMARY

A panel fastener according to the present disclosure is part of a building system such as a ceiling or wall. In particular embodiments, the fastener is provided with a large washer-type head and a central shank that controls the depth to which the fastener can be driven. These features in conjunction with high-low threads provide a unique fastener that easily and quickly secures an easily compressed building panel to a structure without damaging the panel.

In one aspect, a panel fastener extends along a central axis and includes a head having a first surface and a second surface opposite the first surface; an engagement feature on the first surface of the head, the engagement feature being configured to be engaged by a driving tool; a shank extending from the second surface of the head; a threaded portion extending from the shank, the threaded portion having first and second helical threads arranged in an intertwined manner; the first thread extending farther radially from the central axis than does the second thread; and the central shank being located between the head and the threaded portion.

In another aspect, the shank is a cylinder having a shank diameter, the shank diameter being constant over the entire length of the shank.

In another aspect, the shank diameter is larger than an outer diameter of the first thread.

In another aspect, a ratio of the shank diameter to the outer diameter of the first thread is in a range of 1:1 to 2:1.

In another aspect, a ratio of the shank diameter to the outer diameter of the first thread is in a range of 1.11:1 to 1.83:1.

In another aspect, the shank has a first end that is adjacent to the threaded portion, and the first end of the shank is flat and extends in a plane that is perpendicular to the central axis.

In another aspect, the second side of the head is flat and extends in a plane that is perpendicular to the central axis.

In another aspect, the first side of the head is flat and extends in a plane that is perpendicular to the central axis.

In another aspect, the head has a thickness in a direction parallel to the central axis, the head has a diameter, and a ratio of the thickness of the head to the diameter of the head is in a range of 1:20 to 1:5.

In another aspect, the ratio of the thickness of the head to the diameter of the head is in a range of 1:13 to 1:8.

In another aspect, a ratio of the shank diameter to the diameter of the head is in a range of 1:10 to 1:2.

In another aspect, the ratio of the shank diameter to the diameter of the head is in a range of 1:5 to 1:3.

In another aspect, the shank has a shank length, the threaded portion has a threaded portion length, and the threaded portion length is less than the shank length.

In another aspect, the threaded portion is self-tapping.

In another aspect, an end surface of the shank forms an annular shoulder at a proximal end of the threaded portion, and the first and second helical threads of the threaded portion extend from the end surface of the shank In another aspect, a panel fastener includes a head having a first surface and a second surface opposite the first surface; an engagement feature on the first surface of the head, the engagement feature configured to be engaged by a driving tool; a shank extending from a first end to a second end; a threaded portion extending from a first end to a second end, the threaded portion comprising a central shaft that extends along a longitudinal axis, and one or more helical threads extending radially from the central shaft; the second surface of the head forming a first annular shoulder at the second end of the shank and the first end of the shank having an end surface that forms a second annular shoulder at the second end of the threaded portion; and wherein the shank has a substantially constant transverse cross-section for a substantially entire length from the end surface of the shank to the first annular shoulder.

In another aspect, the one or more helical threads of the threaded portion extend from the end surface of the shank.

In another aspect, the shank has a smooth outer surface that is free of texture and protuberances.

In another aspect, each of the second surface of the head and the end surface of the shank is orthogonal to the central axis.

In another aspect, the shank has a shank length measured from the first end of the shank to the second end of the shank; the threaded portion has a threaded portion length measured from the first end of the threaded portion to the second end of the threaded portion; and wherein the shank length is greater than the threaded portion length.

In another aspect, a ratio of the shank length to the threaded portion length is in a range of 1.25:1 to 2:1.

In another aspect, the one or more threads of the threaded portion have a maximum outer diameter and the shank has a shank diameter, the shank diameter being greater than the maximum outer diameter of the one or more threads of the threaded portion.

In another aspect, a ratio of the shank diameter to the maximum outer diameter of the one or more threads is in a range of 1:1 to 2:1.

In another aspect, a ratio of the shank diameter to the maximum outer diameter of the one or more threads is in a range of 1.11:1 to 1.83:1.

In another aspect, the threaded portion has first and second helical threads arranged in an intertwined manner; and the first thread extends farther radially from the central axis than does the second thread.

In another aspect, an end surface of the shank forms an annular shoulder at a proximal end of the threaded portion, and the one or more helical threads of the threaded portion extend from the end surface of the shank.

In another aspect, a panel fastener extending along a central axis includes a head having a first surface and a second surface opposite the first surface; an engagement feature on the first surface of the head, the engagement feature configured to be engaged by a driving tool; a shank extending from the second surface of the head to an end surface; a threaded portion extending from the end surface of the shank, the threaded portion comprising a central shaft and one or more helical threads extending radially from the central shaft; and the end surface of the shank forming an annular shoulder at a proximal end of the threaded portion, the one or more threads, the one or more helical threads of the threaded portion extending from the end surface of the shank.

In another aspect, the threaded portion has first and second helical threads arranged in an intertwined manner; and the first thread extends farther radially from the central axis than does the second thread.

In another aspect, the shank is a cylinder having a shank diameter, the shank diameter being constant over the entire length of the shank.

In another aspect, a building panel system includes a building panel having a thickness; a panel fastener extending along a central axis, the panel fastener includes a head having a first surface and a second surface opposite the first surface; an engagement feature on the first surface of the head, the engagement feature configured to be engaged by a driving tool; a shank extending from the second surface of the head to an end surface; a threaded portion extending from the end surface of the shank, the threaded portion comprising a central shaft and one or more helical threads extending radially from the central shaft; and the shank having a shank length measured from the second surface of the head to the end surface; the shank length being less than or equal to the thickness of the building panel; and the panel fastener secures the building panel to a structure.

In another aspect, a ratio of the shank length to the thickness of the building panel is in a range of 0.9:1 to 1:1.

In another aspect, a ratio of the shank length to the thickness of the building panel is in a range of 0.95:1 to 1:1.

In another aspect, the shank is a cylinder having a shank diameter, the shank diameter being constant over the entire length of the shank.

In another aspect, the threaded portion has first and second helical threads arranged in an intertwined manner; and the first thread extends farther radially from the central axis than does the second thread.

In another aspect, an end surface of the shank forms an annular shoulder at a proximal end of the threaded portion, and the one or more helical threads of the threaded portion extend from the end surface of the shank.

In another aspect, a building panel system includes a building panel having a thickness; a plurality of the panel fastener according to this disclosure; and the plurality of panel fasteners secure the building panel to a structure.

In another aspect, the building panel system includes the structure to which the panel fastener attaches the building panel.

In another aspect, the structure is a furring strip.

In another aspect, the shank length is less than or equal to the thickness of the panel.

In another aspect, a ratio of the shank length to the thickness of the panel is in a range of 0.9:1 to 1:1.

In another aspect, a ratio of the shank length to the thickness of the panel is in a range of 0.95:1 to 1:1.

In another aspect, the shank length is equal to the thickness of the panel.

In another aspect, in an assembled state, the shank extends through the entire thickness of the building panel, the head is located on a first side of the building panel, the threaded portion is located on a second side of the building panel, the threaded portion is located outside of the building panel, and the threaded portion penetrates the structure.

In another aspect, the building panel is made of a fibrous material.

In another aspect, the building panel system is a ceiling system and the building panel is a ceiling panel.

In another aspect, the building panel system is a wall system and the building panel is a wall panel.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

Figure 1:
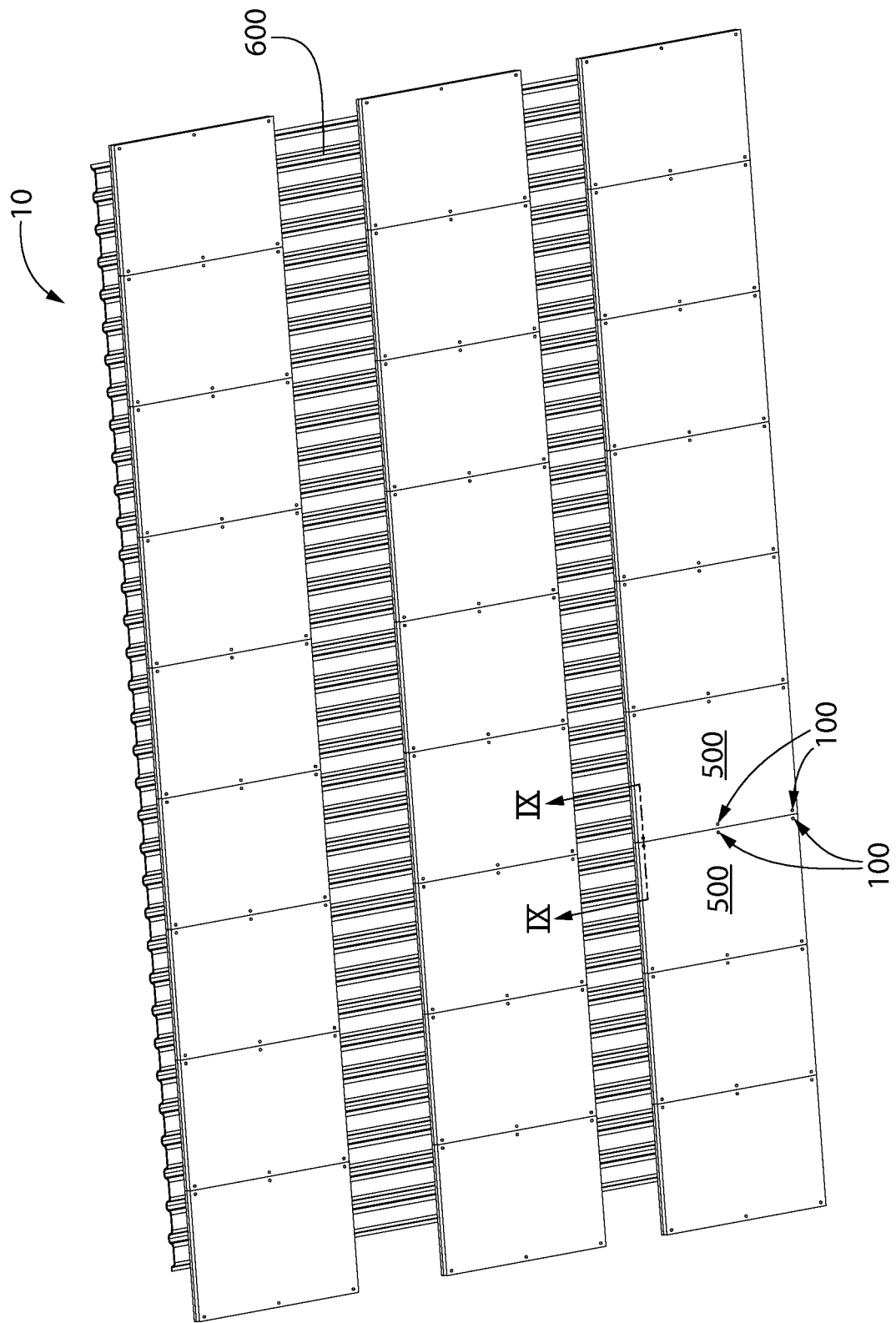
FIG. 1 is a perspective view of ceiling system in accordance with exemplary embodiments of the invention.

All drawings are schematic and not necessarily to scale. Parts given a reference numerical designation in one figure may be considered to be the same parts where they appear in other figures without a numerical designation for brevity unless specifically labeled with a different part number and described herein.

DETAILED DESCRIPTION

The following description of the preferred embodiment(s) is merely exemplary in nature and is in no way intended to limit the invention, its application, or uses.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "connected," "coupled," "interconnected," and similar refer to a relationship wherein structures are secured or attached to one another either directly or indirectly through intervening structures, as well as both movable or rigid attachments or relationships, unless expressly described otherwise. The term "fixed" refers to two structures that cannot be separated without damaging one of the structures. The term "filled" refers to a state that includes completely filled or partially filled.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

An example of a ceiling system 10 in accordance with embodiments of the invention is shown in FIG. 1. Although a ceiling system is shown in FIG. 1, it is noted that the invention and the following description also apply to a wall system or any other system using panels. As such, the following embodiments and descriptions may refer to just a ceiling system or a wall system, but it is understood that these embodiments and descriptions apply to all building panel systems.

In the embodiment shown in FIG. 1, ceiling system 10 includes a plurality of ceiling panels 500 that are secured to a corrugated metal deck 600 by a plurality of fasteners 100. In some embodiments panels 500 are attached directly to metal deck 600, and in other embodiments panels 500 are attached to a furring strip (discussed below) which are in turn attached to metal deck 600. Although metal deck 600 with furring strips is the structure used in this example, it is noted that panels 500 can be attached to other structures as well. Non-exclusive examples of structures to which panels 500 can be attached include beams, rafters, or joists made of wood, metal, composites, or any other material into which a screw can be driven. The locations of fasteners 100 shown in FIG. 1 are examples only and are not limiting. In some examples, fasteners 100 are located between 4 and 6 inches from the edges of panels 500.

Ceiling panels 500 can be, for non-exclusive example, a fibrous or other acoustical panel, a fabric covered panel, or any other compressible panel.

Ceiling panels 500 may comprise a body having an upper surface opposite a lower surface and a body side surface that extends between the upper surface and the lower surface, thereby defining a perimeter of the body. The body may have a body thickness that extends from the upper surface to the lower surface. The body thickness may range from about 12 mm to about 40 mm—including all values and sub-ranges there-between.

The body of ceiling panel 500 may be porous, thereby allowing airflow through the body between the upper surface and the lower surface. The body may be comprised of a binder and fibers. Non-limiting examples of binder may include a starch-based polymer, polyvinyl alcohol (PVOH), a latex, polysaccharide polymers, cellulosic polymers, protein solution polymers, an acrylic polymer, polymaleic anhydride, epoxy resins, or a combination of two or more thereof. The fibers may be organic fibers, inorganic fibers, or a blend thereof. Non-limiting examples of inorganic fibers mineral wool (also referred to as slag wool), rock wool, stone wool, and glass fibers. Non-limiting examples of organic fiber include fiberglass, cellulosic fibers (e.g. paper fiber—such as newspaper, hemp fiber, jute fiber, flax fiber, wood fiber, or other natural fibers), polymer fibers (including polyester, polyethylene, aramid—i.e., aromatic polyamide, and/or polypropylene), protein fibers (e.g., sheep wool), and combinations thereof. Depending on the specific type of material, the fibers may either be hydrophilic (e.g., cellulosic fibers) or hydrophobic (e.g. fiberglass, mineral wool, rock wool, stone wool). The fibers may be present in an amount ranging from about 5 wt. % to about 99 wt. % based on the total dry weight of the body—including all values and sub-ranges there-between. In some embodiments, the body may further comprise a filler and/or additive. Non-limiting examples of filler may include powders of calcium carbonate, including limestone, titanium dioxide, sand, barium sulfate, clay, mica, dolomite, silica, talc, perlite, polymers, gypsum, wollastonite, expanded-perlite, calcite, aluminum trihydrate, pigments, zinc oxide, or zinc sulfate. The filler may be present in an amount ranging from about 25 wt. % to about 99 wt. % based on the total dry weight of the body 120—including all values and sub-ranges there-between. The body may be treated with a hydrophobic component thereby rending the body stain-repellant.

FIGS. 2-6 show an exemplary fastener 100 in accordance with embodiments of the invention. Fastener 100 has a head 200 and a threaded portion 400 that are connected by a centrally positioned shank 300. The shank 300 extends along a longitudinal axis that intersects the head 200 and the threaded portion 400.

Head 200 is, in this example, a flat washer-like element that is significantly larger in diameter than it is thick. Head 200 has a large flat upper surface 210 or radius R1 and a similar lower surface 220. Other shapes can be used for upper surface 210 and lower surface 220 such as, for non-exclusive example, concave surfaces, convex surfaces, partial concave surfaces, and partial convex surfaces. In addition, upper surface 210 and lower surface 220 can be parallel or non-parallel whether the surfaces are planar or non-planer. In this example, upper surface 210 and lower surface 220 are planar and parallel and a flat vertical edge 230 of thickness T1 connects upper surface 210 and lower surface 220. The flat washer-like shape that is significantly larger in diameter than it is thick provides a large bearing surface on its lower side (lower surface 220) that distributes force over a much larger area than does a conventional screw. As a result, a lower pressure is exerted on the ceiling panel by fastener 100, which is especially advantageous when the ceiling panel is easily compressible and therefore easily damaged by deformation.

In particular embodiments, the ratio of the thickness T1 of head 200 to the diameter 2R1 of head 200 is in a range of 1:20 to 1:5—including all ratios and sub-ranges there-between. In particular embodiments, the ratio of the thickness T1 of head 200 to the diameter 2R1 of head 200 is in a range of 1:14 to 1:9—including all ratios and sub-ranges there-between. In particular embodiments, the ratio of the thickness T1 of head 200 to the diameter 2R1 of head 200 is in a range of 1:9 to 1:11—including all ratios and sub-ranges there-between. A smaller thickness T1 relative to the diameter of head 200 can result in a less obtrusive and visible fastener 100 in the installed state.

The diameter 2R1 of the head may range from about 0.5 to about 1.0 inch—including all diameters and sub-ranges there-between. In some embodiments, the diameter 2R1 of the head may range from about 0.5 to about 0.7 inch—including all diameters and sub-ranges there-between. In some embodiments, the diameter 2R1 of the head may range from about 0.55 to about 0.65 inch—including all diameters and sub-ranges there-between.

The thickness T1 of the head may range from about 0.05 to about 0.1 inch—including all diameters and sub-ranges there-between. In some embodiments, the diameter 2R1 of the head may range from about 0.055 to about 0.09 inch—including all diameters and sub-ranges there-between. In some embodiments, the thickness T1 of the head may range from about 0.055 to about 0.065 inch—including all thicknesses and sub-ranges there-between. In other embodiments, the Examples of the invention have a head having a diameter 2R1 of about 0.55 inch to about 0.65 inch and a thickness ranging from about 0.055 to about 0.065 inch—including all diameters and thickness there-between, as well as all sub-ranges there-between.

In particular embodiments, the ratio of the diameter of shank 300 to the diameter of head 200 is in a range of 1:10 to 1:3. In particular embodiments, the ratio of the diameter of shank 300 to the diameter of head 200 is in a range of 1:5 to 1:3—including all ratios and sub-ranges there-between. In particular embodiments, the ratio of the diameter of shank 300 to the diameter of head 200 is in a range of 1:4 to 1:3—including all ratios and sub-ranges there-between.

Examples of the invention have a shank having a diameter 2R2 of between 0.1 and 0.3 inch and a length L of between 0.6 and 0.8 inch—including all diameters and lengths, as well as sub-ranges there-between. In some embodiments, the shank may have a diameter 2R2 of between 0.15 and 0.25 inch and a length of between about 0.65 and about 0.72 inch—including all diameters and lengths, as well as sub-ranges there-between. In some embodiments, the shank may have a diameter of between about 0.175 and about 0.185 inch and a length of between about 0.67 and about 0.69 inch—including all lengths and diameters and sub-ranges there-between.

The ratio of the diameter of shank 300 to the length L of the shank 300 may be in a range of 1:2 to 1:5—including all ratios and sub-ranges there-between. In particular embodiments, the ratio of the diameter of shank 300 to the length L of the shank 300 is in a range of 1:2 to 1:4—including all ratios and sub-ranges there-between. In particular embodiments, the ratio of the diameter of shank 300 to the length L of the shank 300 is in a range of 1:3 to 1:4—including all ratios and sub-ranges there-between.

In the example shown in FIGS. 2-6, head 200 includes a driving feature 240 that provides an interface between fastener 100 and a driving tool. In this example driving feature 240 is configured to accommodate a phillips-head screwdriver. However, driving feature 240 can be shaped to accommodate any appropriate driving tool such as, for non-exclusive example, a flat-head screwdriver, a torx bit, or an allen wrench. Because head 200 and driving feature 240 can be visible in the finished ceiling system, it is desirable to make driving feature 240 as small and inconspicuous as possible while still providing sufficient engagement with the appropriate driving tool.

Figures 2, 3:
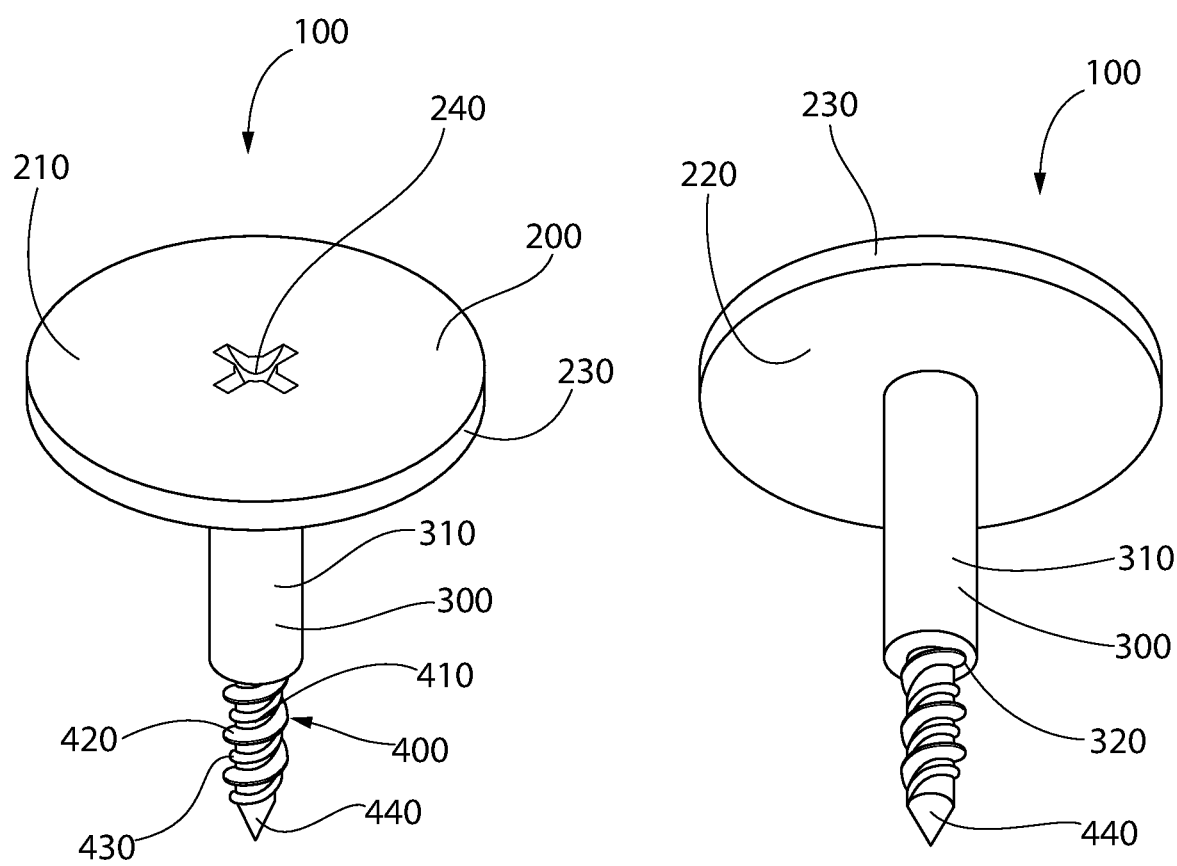
FIG. 2 is an upper perspective view of a multi-featured panel fastener in accordance with exemplary embodiments of the invention.
FIG. 3 is a lower perspective view of the multi-featured panel fastener shown in FIG. 2.
Figure 5:
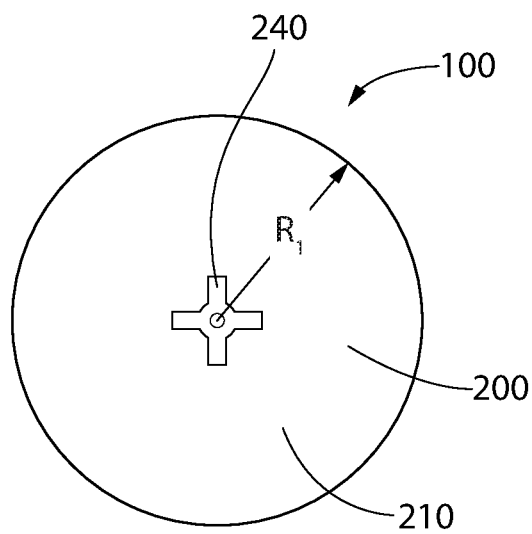
FIG. 5 is a top view of the multi-featured panel fastener shown in FIGS. 2-4.
Figure 4:
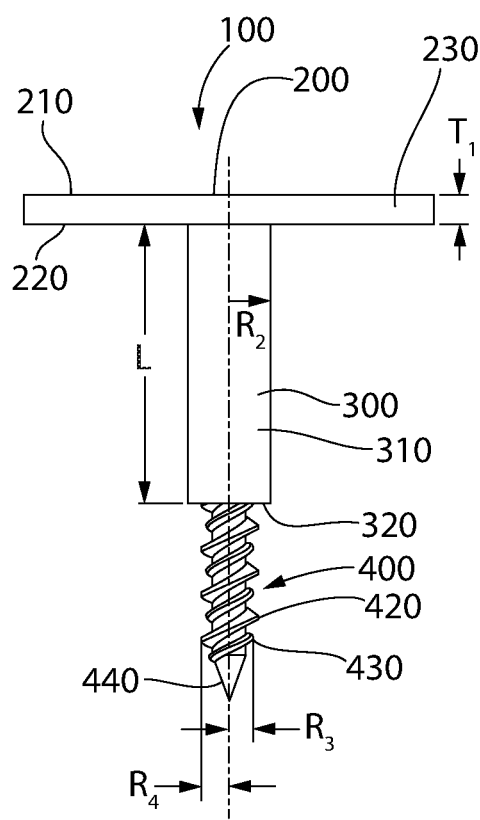
FIG. 4 is a side view of the multi-featured panel fastener shown in FIGS. 2 and 3.
Figure 6:
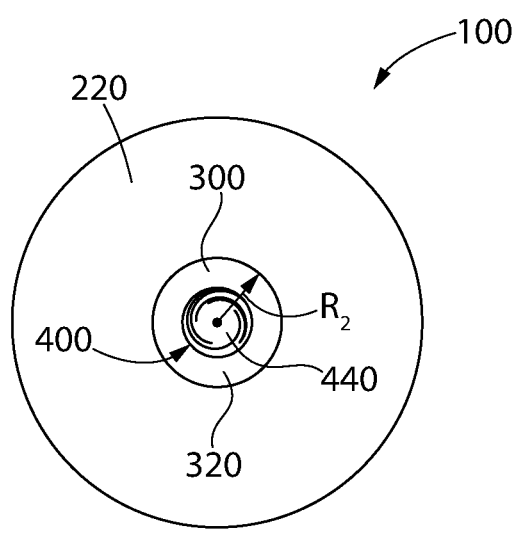
FIG. 6 is a bottom view of the multi-featured panel fastener shown in FIGS. 2-5.

Shank 300 extends from lower surface 220 of head 200, as shown in FIGS. 2-4 and is, in this example, a smooth, non-threaded cylinder having a surface 310. Shank 300 has a length L that is related to the thickness of the ceiling panels that are to be held in place by fastener 100. Examples of thicknesses of panels 500 are ½", ¾", and 1". However, any panel thickness can be accommodated by sizing shank length L appropriately. At the end of shank 300 that is opposite head 200, an abutting surface 320 is provided. Abutting surface 320 extends radially from threaded portion 400 as shown in FIGS. 3, 4 and 6. In this example, abutting surface 320 is a planar round surface of radius R2 that is perpendicular to a central axis of fastener 100. Abutting surface 320 provides a stop (explained further below) that limits how far threaded portion 400 can advance into the structure to which fastener 100 is connected.

In particular embodiments, length L of shank 300 is equal to the thickness of the ceiling panels. This configuration allows lower surface 220 of head 200 to contact the outer surface of the panel and exert force of the outer surface of the panel without allowing head 200 to press into the outer surface of the panel. If the thickness of the panel and the length L of shank 300 are very precise, then this configuration can provide secure fastening without damaging the panel. However, if the thickness of some or all of the panels in a system is just slightly less than length L of shank 300, then those panels can possibly move relative to fastener 100 and the structure. Such movement can be detrimental in that it can cause damage to the panel over time and can generate noise as the panel loses and regains contact with head 200 and/or the structure. In addition, such movement can be visible from the occupied space below the ceiling system. Changes in airflow and other factors can cause such movement.

In particular embodiments, length L of shank 300 is slightly less than the thickness of the ceiling panels. This configuration assures that lower surface 220 of head 200 will contact the outer surface of the panel and exert force of the outer surface of the panel when abutting surface 320 is in contact with the structure. This provides a secure attachment that prevents movement of the panel relative to the structure. However, this configuration can result in head 200 pressing slightly into the outer surface of the panel. The strength of the panel material and the difference in length L and the thickness of the panel will dictate the extent (if any) to which lower surface 220 of head 200 deforms the outer surface of the panel when abutting surface 320 is in contact with the structure. For example, length L can be 1/32" less, 1/16" less, or any amount less than the thickness of the ceiling panels. The height of the ceiling system above the occupants of the occupied space, lighting, and other factors should be considered when determining the acceptable amount of deformation.

In particular embodiments, the ratio of the shank length to the thickness of the panel is between 0.9:1 and 1:1. In particular embodiments, the ratio of the shank length to the thickness of the panel is between 0.95:1 and 1:1. Examples of the invention have a shank length of between 0.678 and 0.698 inches for use with a panel having a nominal thickness of 0.75 inches.

In particular embodiments where length L of shank 300 is less than the thickness of the panel, thickness T1 of head 200 can have a relationship to the difference of the thickness of the panel, TP, and length L of shank 300 that results in upper surface 210 of head 200 being located slightly above an upper surface of the panel while lower surface 220 of head 200 is located slightly below the upper surface of the panel. In some embodiments, the ratio of T1 to TP-L can be between slightly greater than 1:1 to 3:1. In other embodiments, the ratio of T1 to TP-L can be between slightly greater than 1:1 to 2:1. The lower end of this range of ratios is slightly greater than 1:1 in order for upper surface 210 of head 200 to be located slightly above the upper surface of the panel.

In other embodiments, the ratio of T1 to TP-L is 1:1 (in other words, TI+L=TP), which results in upper surface 210 of head 200 being parallel to the upper surface of the panel. In other embodiments, the ratio of T1 to TP-L is less than 1:1 (in other words, TI+L<TP), which results in upper surface 210 of head 200 being below the upper surface of the panel.

A larger difference between the shank diameter and the head diameter creates a large lower surface 220 of head 200 and, therefore, provides more bearing surface to help prevent deformation and/or breaking of the panel surface.

Threaded portion 400 extends from abutting surface 320 as shown, for example, in FIGS. 2-4 and 6-8. In FIGS. 2-4 and 6, the threaded portion 400 has two separate helical threads 420, 430 that extend from a central portion 410 in a double helix formation. In the example shown, threads 420, 430 form high-low threads in that thread 420 is a high thread and thread 430 is a low thread. High thread 420 has a thread radius R4 that is larger than thread radius R3 of low thread 430 (see FIG. 4). In other examples, the two separate helical threads have the same thread radius and are, therefore, the same height.

Figure 4A:
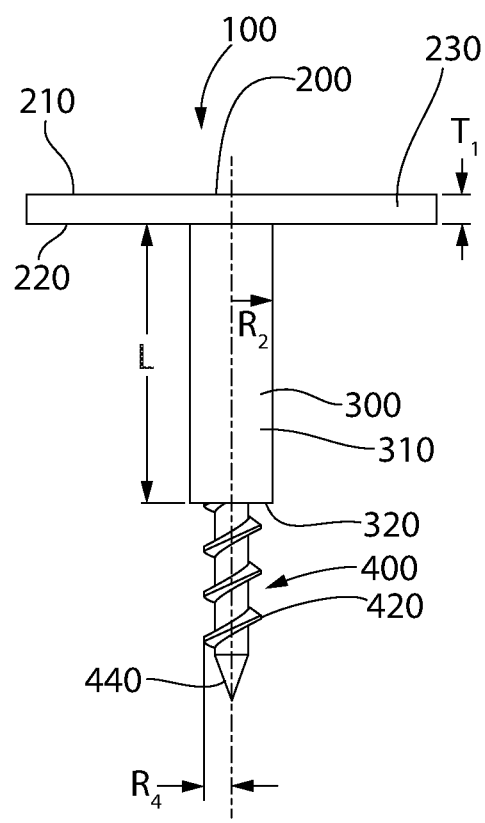
FIG. 4A is a side view of the multi-featured panel fastener according to another embodiment of the present invention.
Figure 7:
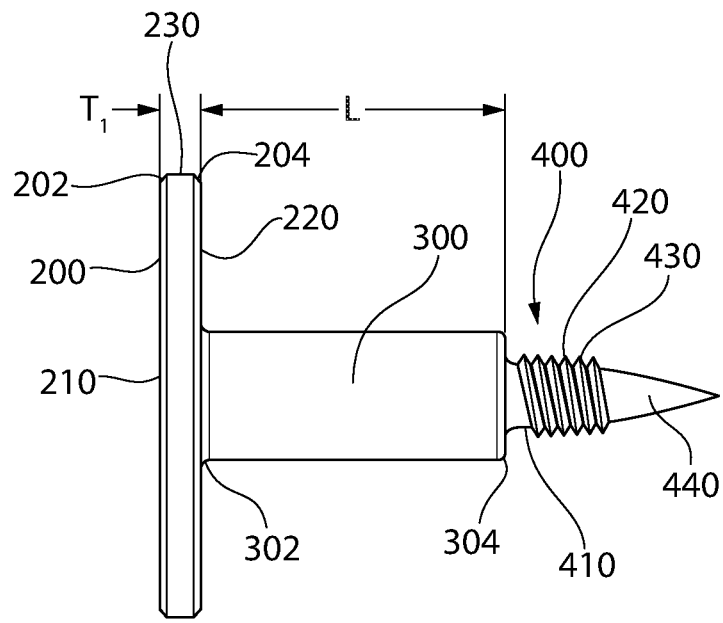
FIG. 7 is a side view of a multi-featured panel fastener in accordance with exemplary embodiments of the invention.
Figure 8:
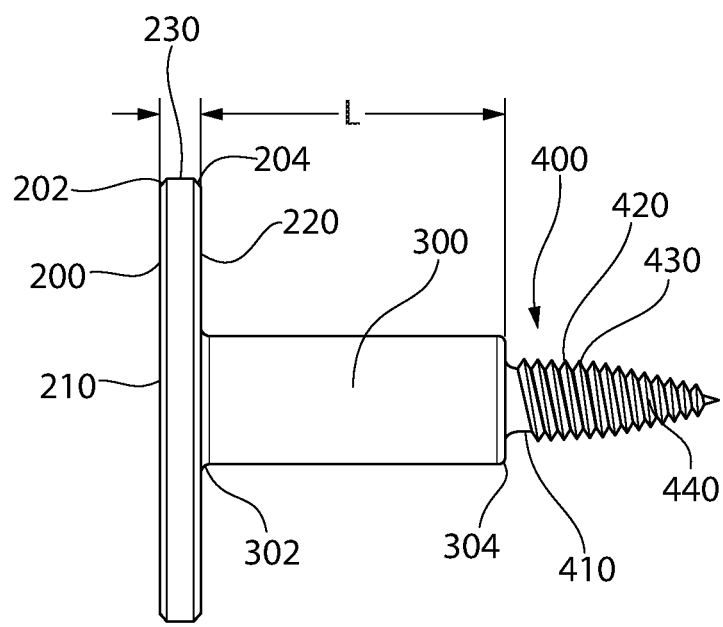
FIG. 8 is a side view of a multi-featured panel fastener in accordance with exemplary embodiments of the invention.

As shown in FIGS. 4A, 7, and 8, the threaded portion 400 may comprise thread 420 that is a single thread. The single thread may extend outward radially from the central axis. In some embodiments, the single thread 420 may have a thread radius that is equal to the high thread radius R4 of the previous embodiment. According to this embodiment, the single thread 420 may be uniform extending from the abutting surface 320 along the threaded portion 400 until reaching the pointed section 440.

In other embodiments, the single thread of FIGS. 7 and 8 may have a thread radius that is reduced in size with distance from the abutting surface 320 of the shank 300. The thread radius of this embodiment may be equal to the low thread radius R3 of the previous embodiment.

Central portion 410 ends, in this example, in a pointed section 440. Pointed section 440 can be a self-tapping shape that, when driven by, for example, a power screw gun, cuts a hole in the structure to which fastener 100 is fastened. The pointed section 440 may have a generally symmetric conical shape that terminates at apex (also referred to as a conical tip). The apex of the conical tip intersects the longitudinal axis, and a conical wall of the conical tip of the pointed section 440 may be oriented relative to the longitudinal axis at a tip angle ranging from about 20° to about 60°—including all tip angles and sub-ranges there-between. In some embodiments, the tip angle may range from about 20° to about 30°—including all angles and sub-ranges there-between. In some embodiments, the tip angle may range from about 24° to about 28°—including all angles and sub-ranges there-between, preferably about 26°.

Referring now to FIG. 4A, although not shown, the single thread 420 may extend entirely along the threaded section 400 such that it continues along the pointed section 440 and tapers along a wall of the conical tip of the pointed section 440 until it reaches the apex of the conical tip. In such embodiment, the screw may be a self-piercing screw, whereby the single thread 420 that extends to along the conical wall to the apex of conical tip tapers at the tip angle.

According to the embodiments where the threaded portion 400 has two separate helical threads comprising two lead threads (one on each thread), the fastener may facilitate starting of fastener 100 in multiple types of materials. In addition, the existence of low thread 430 creates a larger gap between high threads 420 at or near thread radius R4, which can result in increased holding force in certain materials as compared to a single thread having a pitch equal to twice the thread pitch of high thread 420. This configuration is beneficial because low thread 430 provides added holding force in other materials, such as sheet metal, when compared to a single thread having a pitch equal to twice the thread pitch of high thread 420.

In particular embodiments, the ratio of the shank diameter to the diameter of the high thread 420 is in a range of 1:1 to 2:1. In particular embodiments, the ratio of the shank diameter to the diameter of the high thread 420 is in a range of 1:11 to 1.83:1. The ratio of shank diameter 2R2 to thread diameter 2R4 of the high thread 420 can vary depending on the material of the structure and the panel material. A stronger structure material can require a smaller thread diameter 2R4. A more easily crushed panel material can benefit from a smaller shank diameter 2R2. Examples of the invention have a shank diameter of between 0.2 and 0.33 inch and a maximum high thread diameter of 0.18 inch.

Figure 9:
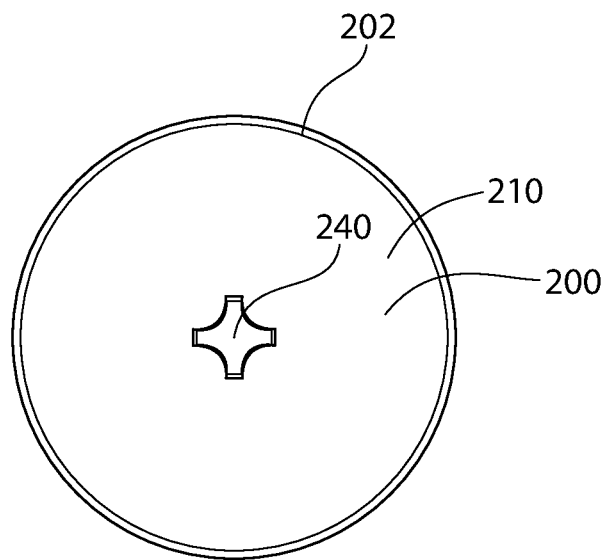
FIG. 9 is a top view of the multi-featured panel fasteners shown in FIGS. 7 and 8.

FIGS. 7-9 show other examples of embodiments of fastener 100. In the examples shown in FIGS. 7-9, head 200 can include a chamfer or radius 202 between upper surface 210 and vertical edge 230, and a chamfer or radius 204 between lower surface 220 and vertical edge 230. Other examples of fastener 100 can include one or both of these chamfers/radiuses.

The examples shown in FIGS. 7 and 8 include a chamfer or radius 302 between lower surface 220 of head 200 and shank 300, and a chamfer or radius 304 at the end of shank 300 adjacent to threaded portion 400. Other examples of fastener 100 can include one or both of these chamfers/radiuses.

In the embodiments shown in FIGS. 7 and 8, shank 300 has a substantially constant transverse cross-section for the substantially entire length from abutting surface 320 of shank 300 to lower surface 220 of head 200.

The examples shown in FIGS. 7 and 8 show two separate helical threads 420, 430 that extend from central portion 410 of threaded portion 400 in a double helix formation. In these examples, helical threads 420, 430 have the same thread radius. However, in other examples, thread 420 and thread 430 have different thread radii. The example shown in FIG. 8 is similar to that shown in FIG. 7, except that threads 420 and 430 in FIG. 8 extend to the end of pointed section 440 of threaded portion 400. The hardness and other qualities of the structure into which fastener 100 will be driven will be considered in determining which whether threads 420 and 430 extend to the end of pointed section 440 or not.

Figure 10:
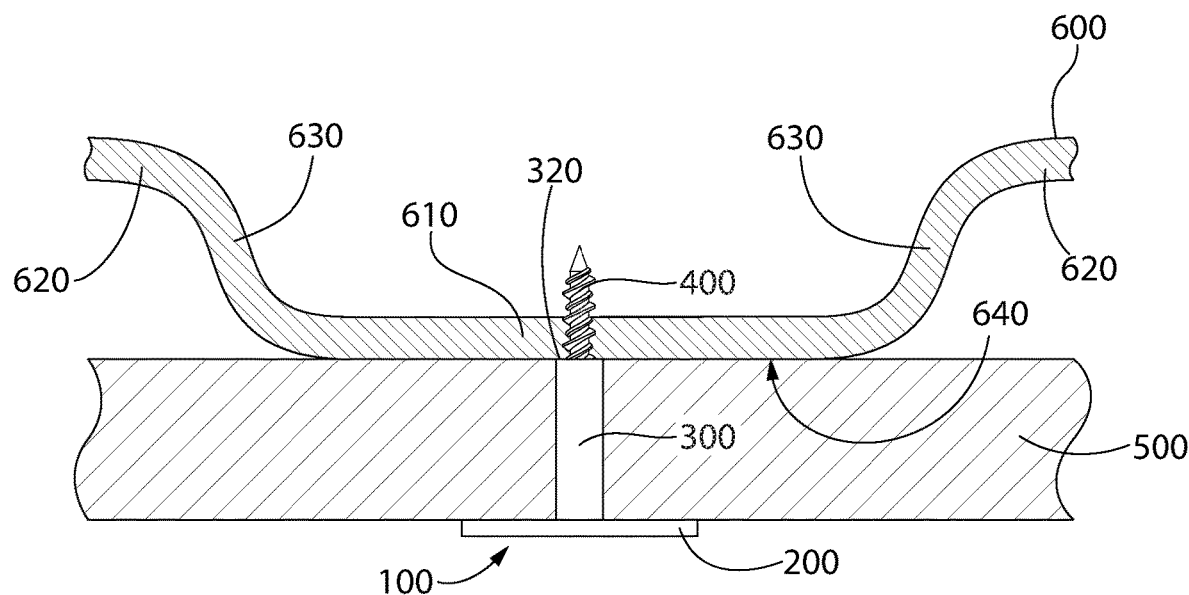
FIG. 10 is a partial sectional view of a panel attached to a structure by a multi-featured panel fastener in accordance with exemplary embodiments of the invention.

FIG. 10 shows an example of fastener 100 attaching panel 500 directly to a corrugated metal deck 600. In this example, corrugated metal deck 600 has an undulating profile created by high section 620, transition sections 630 and low sections 610. An upper surface of panel 500 is pressed against a lower surface 640 of low section 610 by threaded portion 400 engaging low section 610. FIG. 10 shows how abutting surface 320 of shank 300 contacts the structure (in this case, lower surface 640) and prevents head 200 of fastener 100 from being drawn farther into panel 500. If additional driving force is applied to fastener 100 in the condition shown in FIG. 10, abutting surface 320 will stop fastener 100 from progressing any further because abutting surface 320 is in contact with lower surface 640 of corrugated metal deck 600.

Figure 11:
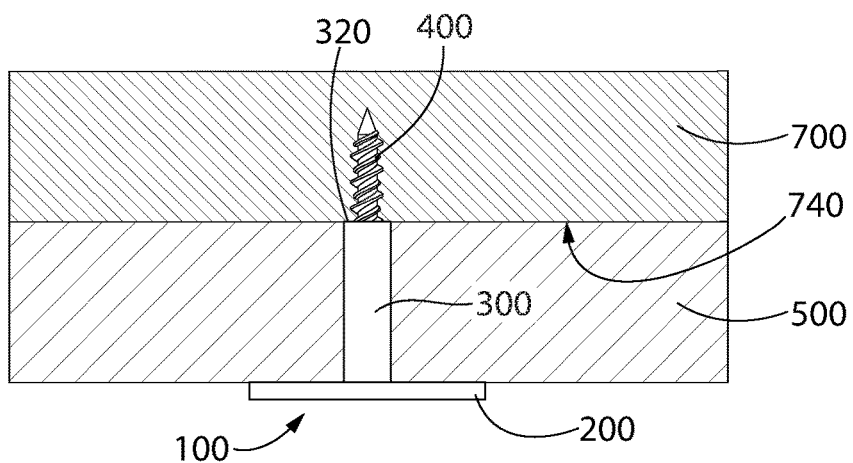
FIG. 11 is a partial sectional view of a panel attached to a structure by a multi-featured panel fastener in accordance with exemplary embodiments of the invention.

FIG. 11 shows an example of fastener 100 attaching panel 500 directly to a furring strip 700. Although furring strip 700 is shown in this example as the structure, other wood or similar structures can also be used. FIG. 11 shows how abutting surface 320 of shank 300 contacts the structure (in this case, lower surface 740 of furring strip 700) and prevents head 200 of fastener 100 from being drawn farther into panel 500. If additional driving force is applied to fastener 100 in the condition shown in FIG. 11, abutting surface 320 will stop fastener 100 from progressing any further because abutting surface 320 is in contact with lower surface 740 of furring strip 700.

Fastener 100 can be coated or uncoated. Non-exclusive examples of coatings include powder coating (or other baked-on coatings), zinc coating, or wet paint. The entire fastener can be coated or just a portion such as, for example, just upper surface 210 or just upper surface 210 and vertical edge 230.

Figure 12:
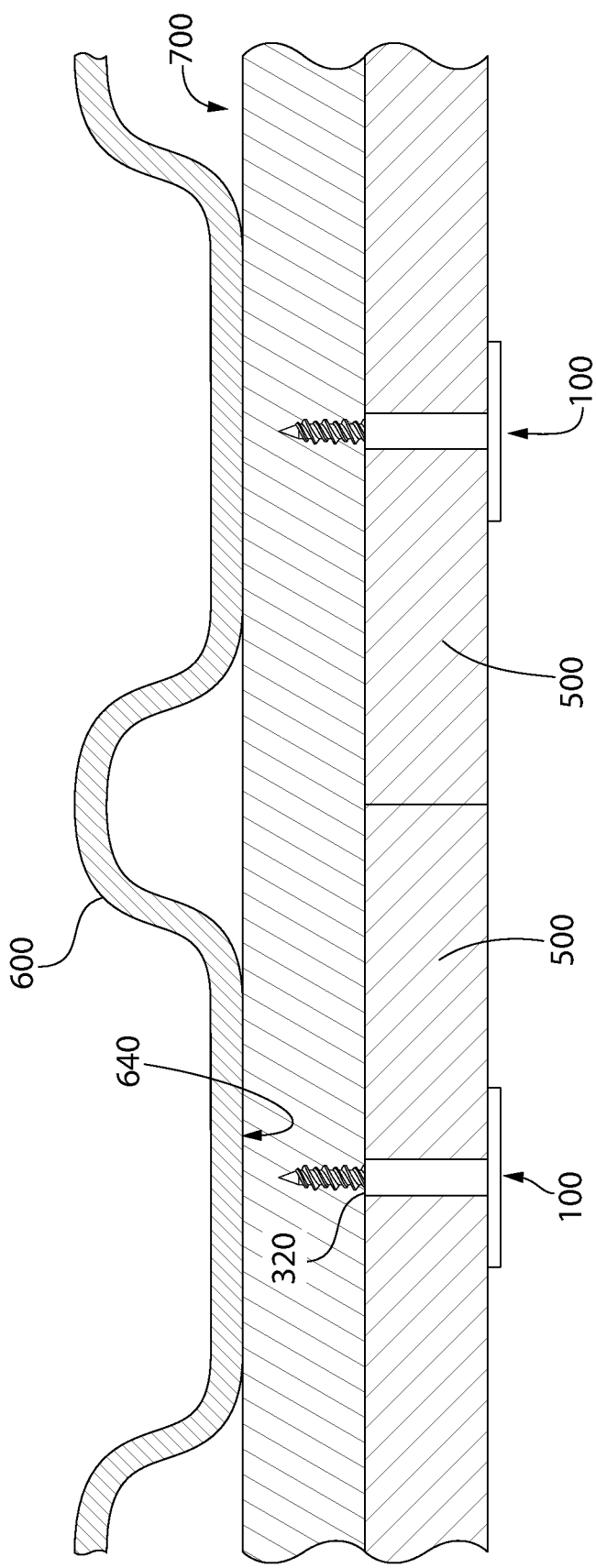
FIG. 12 is a partial sectional view of two panels attached to a structure by a multi-featured panel fastener in accordance with exemplary embodiments of the invention.

FIG. 12 shows an example of fasteners 100 attaching two panels 500 to furring strip 700 which is, in turn, attached to corrugated metal deck 600. This is the condition shown at section line IX-IX on FIG. 1. Two adjacent panels 500 abut each other and are held in place by fasteners 100. The function of abutting surface 320 in this example is the same as described with regard to FIG. 11. Furring strip 700 can be a narrow piece of wood or other material that is attached to corrugated metal deck 600 (or other structure) in order to provide a uniform surface to which panels 500 can be attached. Furring strip 700 can be particularly useful if the underlying structure is concrete or some other material that does not accept threaded fasteners well. In the example of FIGS. 1 and 12, furring strips 700 can be hidden from the view of the occupants of the occupied space by panels 500. This can create the appearance of panels 500 floating below corrugated metal deck 600. Fasteners 100 provide an esthetically pleasing, yet structurally sound, attachment solution that avoids deformation of panels 500.

While the foregoing description and drawings represent exemplary embodiments of the present disclosure, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. In addition, numerous variations in the methods/processes described herein may be made within the scope of the present disclosure. One skilled in the art will further appreciate that the embodiments may be used with many modifications of structure, arrangement, proportions, sizes, materials, and components and otherwise, used in the practice of the disclosure, which are particularly adapted to specific environments and operative requirements without departing from the principles described herein. The presently disclosed embodiments are therefore to be considered in all respects as illustrative and not restrictive. The appended claims should be construed broadly, to include other variants and embodiments of the disclosure, which may be made by those skilled in the art without departing from the scope and range of equivalents. In addition, all combinations of any and all of the features described in the disclosure, in any combination, are part of the invention.

What is claimed is:

1. A panel fastener extending along a central axis, the panel fastener comprising:
    a head having a first surface and a second surface opposite the first surface;
    an engagement feature on the first surface of the head, the engagement feature being configured to be engaged by a driving tool;
    a shank extending from the second surface of the head;
    a threaded portion extending from the shank; and
    the shank being located between the head and the threaded portion, and wherein the shank diameter is larger than an outer diameter of the thread,
    wherein a ratio of the shank diameter to the outer diameter of the thread is in a range of 1.11:1 to 1.83:1.

2. The panel fastener of claim 1, wherein the shank is a cylinder having a shank diameter, the shank diameter being constant over the entire length of the shank.

3. The panel fastener of claim 1, wherein the shank has a first end that is adjacent to the threaded portion, and the first end of the shank is flat and extends in a plane that is perpendicular to the central axis.

4. The panel fastener of claim 1, wherein the second surface of the head is flat and extends in a plane that is perpendicular to the central axis and wherein the first surface of the head is flat and extends in a plane that is perpendicular to the central axis.

5. The panel fastener of claim 1, wherein the head has a thickness in a direction parallel to the central axis, the head has a diameter, and a ratio of the thickness of the head to the diameter of the head is in a range of 1:20 to 1:5.

6. The panel fastener of claim 1, wherein a ratio of the shank diameter to the diameter of the head is in a range of 1:8 to 1:2.

7. The panel fastener of claim 1, wherein the shank has a shank length, the threaded portion has a threaded portion length, and the threaded portion length is less than the shank length.

8. The panel fastener of claim 1, wherein the threaded portion is self-tapping.

9. The panel fastener of claim 1, wherein an end surface of the shank forms an annular shoulder at a proximal end of the threaded portion, and the thread of the threaded portion extend from the end surface of the shank.

10. A panel fastener extending along a central axis, the panel fastener comprising:
a head having a first surface and a second surface opposite the first surface;
an engagement feature on the first surface of the head, the engagement feature configured to be engaged by a driving tool;
a shank extending from a first end to a second end;
a threaded portion extending from a first end to a second end, the threaded portion comprising a central shaft and one or more helical threads extending radially from the central shaft;
the second surface of the head forming a first annular shoulder at the second end of the shank and the first end of the shank having an end surface that forms a second annular shoulder at the second end of the threaded portion; and
wherein the shank has a substantially constant transverse cross-section for a substantially entire length from the end surface of the shank to the first annular shoulder, wherein a ratio of the shank length to the threaded portion length is in a range of 1.25:1 to 2:1.

11. The panel fastener of claim 10, wherein the one or more helical threads of the threaded portion extend from the end surface of the shank, and wherein the shank has a smooth outer surface that is free of texture and protuberances.

12. The panel fastener of claim 10, wherein each of the second surface of the head and the end surface of the shank is orthogonal to the central axis.

13. The panel fastener of claim 10, further comprising:
the shank having a shank length measured from the first end of the shank to the second end of the shank;
the threaded portion having a threaded portion length measured from the first end of the threaded portion to the second end of the threaded portion; and
wherein the shank length is greater than the threaded portion length.

14. The panel fastener of claim 10, wherein the one or more threads of the threaded portion have a maximum outer diameter and the shank has a shank diameter, the shank diameter being greater than the maximum outer diameter of the one or more threads of the threaded portion.

15. The panel fastener of claim 10, wherein a ratio of the shank diameter to the maximum outer diameter of the one or more threads is in a range of 1:1 to 2:1.

16. The panel fastener of claim 10, wherein an end surface of the shank forms an annular shoulder at a proximal end of the threaded portion, and the one or more helical threads of the threaded portion extend from the end surface of the shank.

17. A panel fastener extending along a central axis, the panel fastener comprising:
a head having a first surface and a second surface opposite the first surface;
an engagement feature on the first surface of the head, the engagement feature configured to be engaged by a driving tool;
a shank extending from the second surface of the head to an end surface;
a threaded portion extending from the end surface of the shank, the threaded portion comprising a central shaft and one or more helical threads extending radially from the central shaft; and
the end surface of the shank forming an annular shoulder at a proximal end of the threaded portion, the one or more helical threads of the threaded portion extending from the end surface of the shank,
wherein the threaded portion has first and second helical threads arranged in an intertwined manner; and the first thread extends farther radially from the central axis than does the second thread.

18. The panel fastener of claim 17, wherein the shank is a cylinder having a shank diameter, the shank diameter being constant over the entire length of the shank.

* * * * *